(12) United States Patent
Keller et al.

(10) Patent No.: US 8,926,611 B2
(45) Date of Patent: Jan. 6, 2015

(54) ANGULAR LAG IMPLANT FOR INTRAMEDULLARY NAILS

(75) Inventors: Samuel Keller, Hettingen (CH); Reto Senger, Winterthur (CH); Hermann Stricker, Rifferswil (CH)

(73) Assignee: Zimmer GmbH, Winterthur (CH)

( * ) Notice: Subject to any disclaimer, the term of this patent is extended or adjusted under 35 U.S.C. 154(b) by 880 days.

(21) Appl. No.: 12/558,984

(22) Filed: Sep. 14, 2009

(65) Prior Publication Data

US 2011/0066152 A1   Mar. 17, 2011

(51) Int. Cl.
| | |
|---|---|
| *A61B 17/56* | (2006.01) |
| *A61B 17/58* | (2006.01) |
| *A61F 2/30* | (2006.01) |
| *A61B 17/72* | (2006.01) |
| *A61B 17/74* | (2006.01) |

(52) U.S. Cl.
CPC ........... *A61B 17/725* (2013.01); *A61B 17/7266* (2013.01); *A61B 17/744* (2013.01); *A61B 17/748* (2013.01)
USPC ...................................................... 606/62

(58) Field of Classification Search
CPC ....................................... A61B 17/72–17/748
USPC ......... 606/62–68, 70–71, 280–281, 286–288, 606/305
See application file for complete search history.

(56) References Cited

U.S. PATENT DOCUMENTS

| | | | |
|---|---|---|---|
| 2,441,765 A | 5/1948 | Hopkins | |
| 3,256,877 A * | 6/1966 | Haboush | 606/67 |
| 3,308,812 A | 3/1967 | Gidlund | |
| 3,554,193 A | 1/1971 | Konstantinou | |
| 3,678,925 A * | 7/1972 | Fischer et al. | 606/68 |
| 4,632,101 A * | 12/1986 | Freedland | 606/68 |
| 4,721,103 A * | 1/1988 | Freedland | 606/319 |
| 4,862,883 A * | 9/1989 | Freeland | 606/64 |
| 5,578,035 A | 11/1996 | Lin | |
| 5,749,872 A * | 5/1998 | Kyle et al. | 606/66 |
| 5,871,485 A | 2/1999 | Rao et al. | |
| 5,993,486 A * | 11/1999 | Tomatsu | 623/13.11 |
| 6,007,536 A | 12/1999 | Yue | |
| 6,139,552 A * | 10/2000 | Horiuchi | 606/88 |
| 6,238,126 B1 * | 5/2001 | Dall | 403/114 |
| 7,563,263 B2 * | 7/2009 | Orbay et al. | 606/64 |

(Continued)

FOREIGN PATENT DOCUMENTS

| | | | |
|---|---|---|---|
| CH | 547629 A | 4/1974 | |
| DE | 1130111 B | 5/1962 | |

(Continued)

OTHER PUBLICATIONS

International Search Report published Mar. 17, 2011 in related International Application No. PCT/EP2010/005627.

(Continued)

*Primary Examiner* — Mary Hoffman
*Assistant Examiner* — Michelle C Eckman
(74) *Attorney, Agent, or Firm* — Schwegman Lundberg & Woessner, P.A.

(57) ABSTRACT

An orthopedic assembly for stabilizing a fractured bone. The orthopedic assembly includes a support structure and an anchor. The anchor includes a first portion and a second portion moveably coupled to the first portion to adjust an angular orientation of the anchor relative to the femur.

24 Claims, 10 Drawing Sheets

(56) References Cited

U.S. PATENT DOCUMENTS

| | | | |
|---|---|---|---|
| 7,828,828 B2 * | 11/2010 | Lim et al. | 606/300 |
| 8,617,227 B2 * | 12/2013 | Sucec et al. | 606/328 |
| 2001/0034523 A1 | 10/2001 | Nelson | |
| 2005/0010224 A1 | 1/2005 | Watkins et al. | |
| 2005/0182405 A1 * | 8/2005 | Orbay et al. | 606/69 |
| 2005/0234457 A1 | 10/2005 | James et al. | |
| 2006/0052783 A1 * | 3/2006 | Dant et al. | 606/61 |
| 2006/0122600 A1 * | 6/2006 | Cole | 606/62 |
| 2007/0093840 A1 | 4/2007 | Pacelli et al. | |
| 2007/0099151 A1 | 5/2007 | Ilan et al. | |
| 2007/0162011 A1 * | 7/2007 | Leyden et al. | 606/65 |
| 2007/0233102 A1 * | 10/2007 | Metzinger | 606/62 |
| 2008/0255559 A1 * | 10/2008 | Leyden et al. | 606/62 |
| 2010/0023011 A1 * | 1/2010 | Nakamura | 606/64 |
| 2010/0145397 A1 * | 6/2010 | Overes et al. | 606/319 |
| 2010/0152775 A1 * | 6/2010 | Seifert et al. | 606/249 |
| 2010/0211112 A1 * | 8/2010 | Kuster et al. | 606/290 |
| 2011/0282395 A1 * | 11/2011 | Beyar et al. | 606/301 |
| 2012/0109128 A1 * | 5/2012 | Frigg | 606/64 |

FOREIGN PATENT DOCUMENTS

| | | |
|---|---|---|
| DE | 1992626 U | 8/1968 |
| DE | 2030249 A1 | 12/1971 |
| DE | 2127881 A1 | 12/1971 |
| DE | 4217236 A1 | 11/1993 |
| DE | 29605806 U1 | 8/1996 |
| EP | 0382256 A1 | 8/1990 |
| EP | 1867294 A2 | 12/2007 |
| FR | 2271800 A1 | 12/1975 |
| GB | 1231918 A | 5/1971 |
| GB | 1345644 A | 1/1974 |
| GB | 2090745 A | 7/1982 |
| JP | 8126650 A | 5/1996 |
| JP | 9220235 A | 8/1997 |
| JP | 10052438 A | 2/1998 |
| JP | 11318930 A | 11/1999 |
| JP | 2003024344 A | 1/2003 |
| JP | 2004216056 A | 8/2004 |
| WO | WO93/22982 A1 | 11/1993 |
| WO | WO98/01078 A1 | 1/1998 |
| WO | WO99/42053 A1 | 8/1999 |
| WO | WO2008/067022 A2 | 6/2008 |
| WO | WO2011/029632 A1 | 3/2011 |
| WO | WO-2011029632 | 3/2011 |

OTHER PUBLICATIONS

Brochure—KLS Martin Group—Orthopedics/Traumatology, 2009.

* cited by examiner

FIG_1

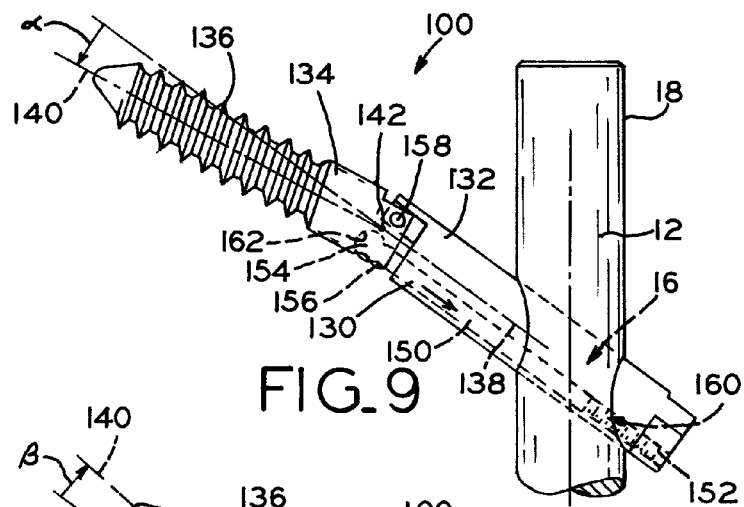
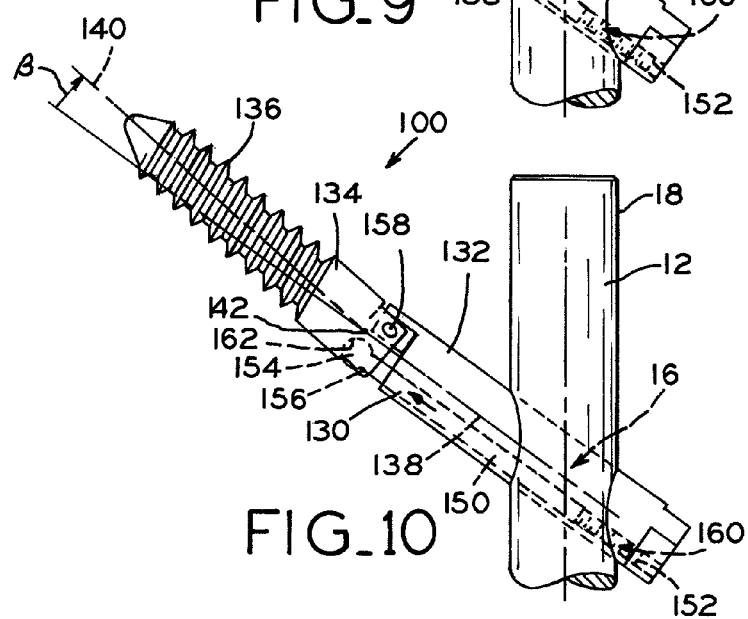
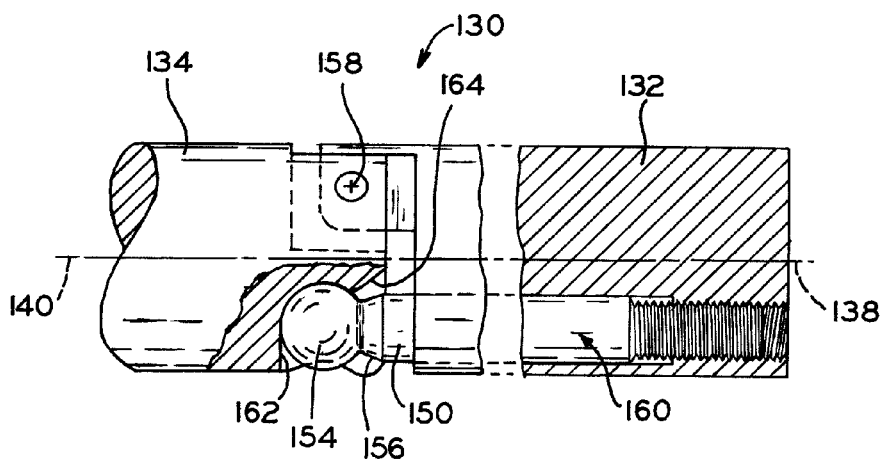

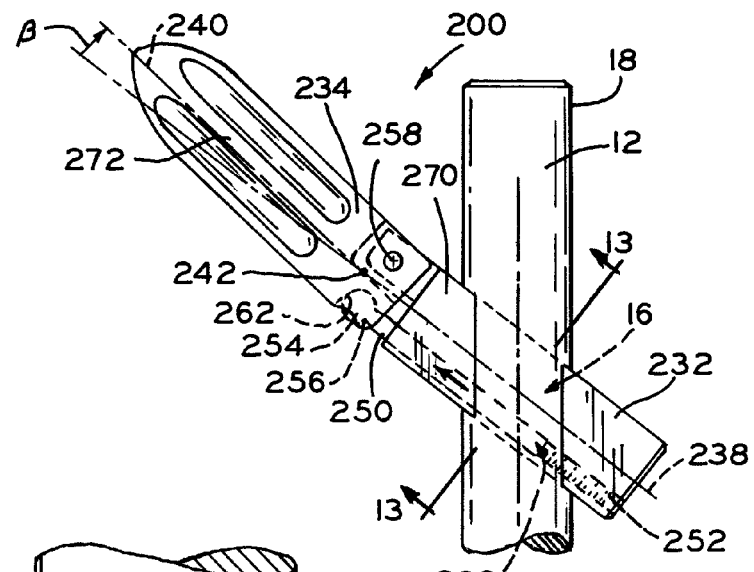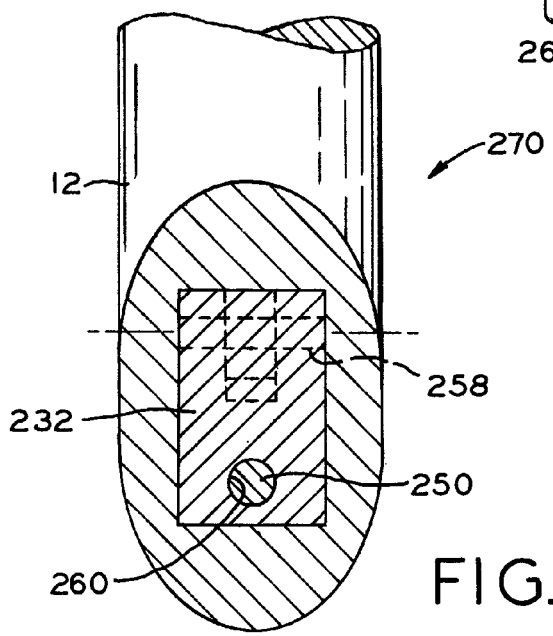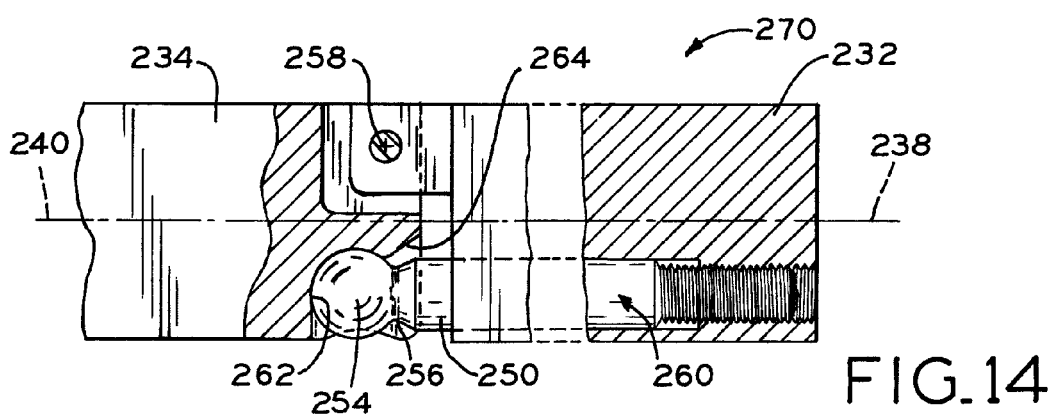

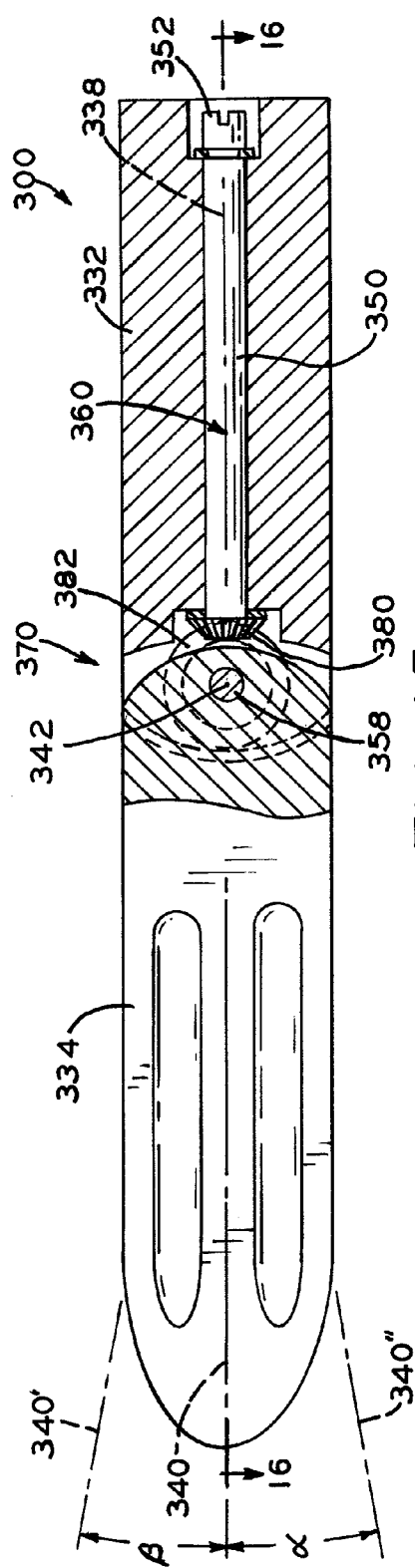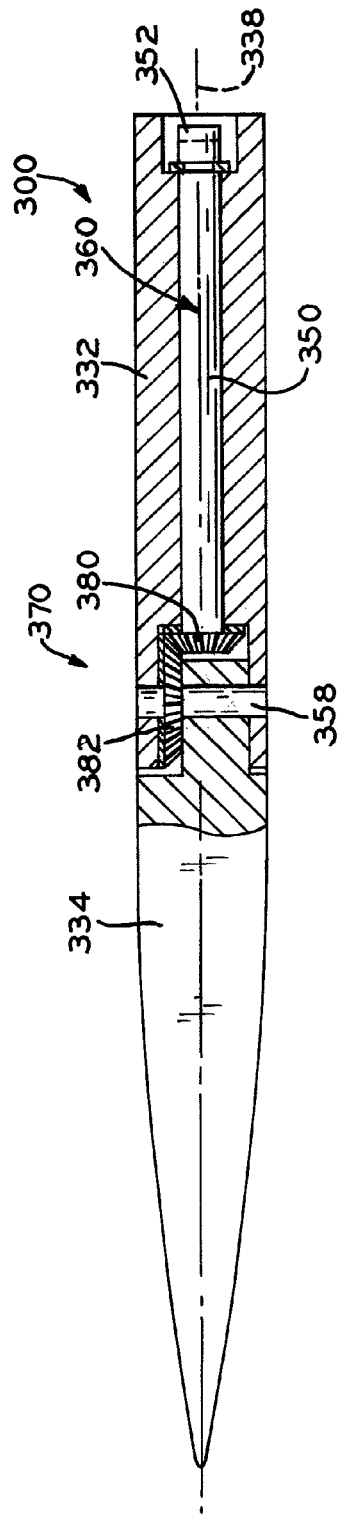

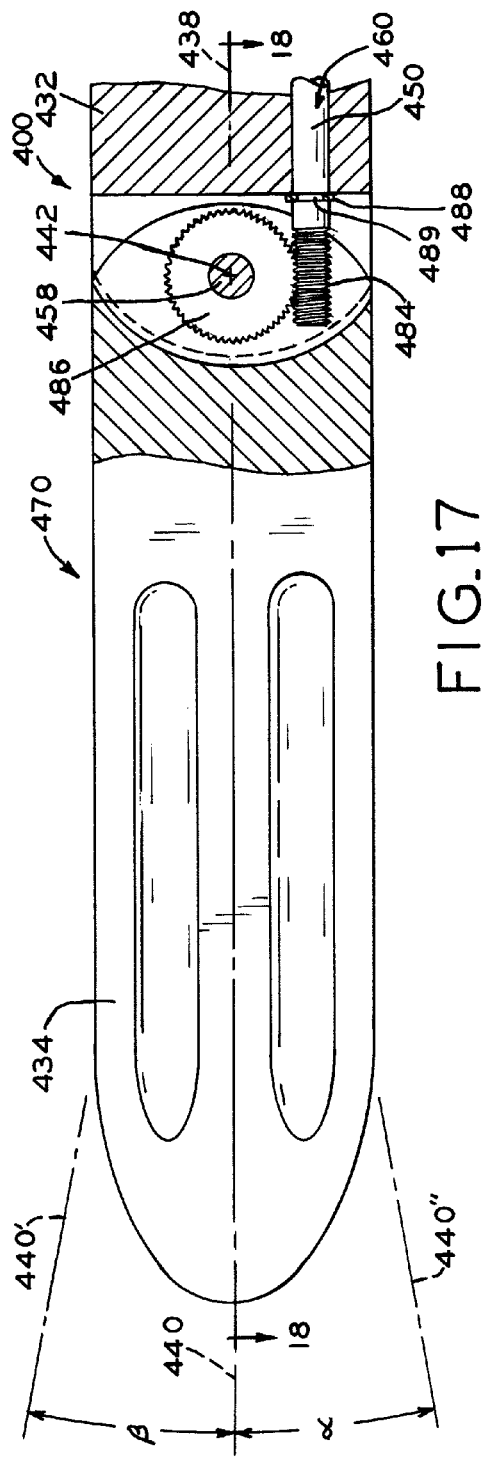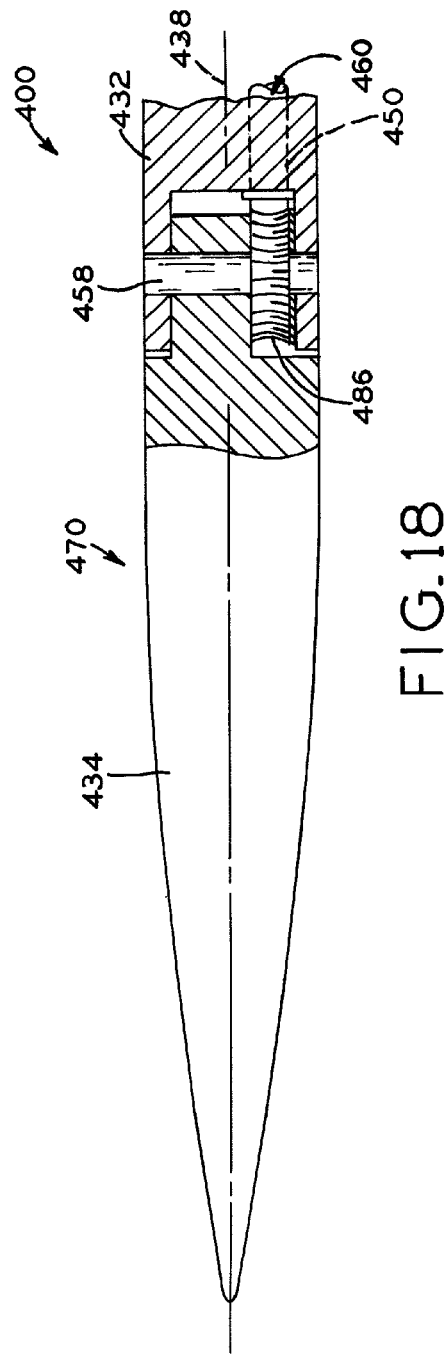

ANGULAR LAG IMPLANT FOR INTRAMEDULLARY NAILS

BACKGROUND

1. Field of the Invention

The present invention relates to an orthopedic assembly. More particularly, the present invention relates to an angular anchor of an orthopedic assembly, and to a method for using the same.

2. Description of the Related Art

An orthopedic assembly may be used to align and stabilize a fracture of a long bone. To align and stabilize a fractured femur, for example, the orthopedic assembly may include an intramedullary nail configured to be driven into a prepared intramedullary canal of the femur and a lag screw that extends through the intramedullary nail and across a fracture line of the femur. For example, if the fracture line is located across the femoral neck, the lag screw may extend through the intramedullary nail, beyond the fracture line, and into the femoral head to secure the femoral head to the femoral shaft.

During the life of the implanted orthopedic assembly, anatomical forces may cause the femoral head to deviate from its proper position relative to the femoral shaft along the fracture line. For example, under a downward anatomical force, the femoral head may collapse relative to the femoral shaft along the fracture line. An optimized alignment of the orthopedic assembly is desired to minimize these undesirable deviations in position.

SUMMARY

The present invention provides an orthopedic assembly for stabilizing a fractured bone. The orthopedic assembly includes a support structure and an anchor. The anchor includes a first portion and a second portion moveably coupled to the first portion to adjust an angular orientation of the anchor relative to the femur.

According to an embodiment of the present invention, an orthopedic assembly is provided that includes a support structure and an anchor. The support structure is configured for securement to a femur, the support structure having an outer periphery and defining a transverse bore that extends through the support structure. The anchor includes a first portion and a second portion, the first portion of the anchor configured to extend through the transverse bore of the support structure and the second portion of the anchor being movably coupled to the first portion of the anchor for movement about at least one pivot axis relative to the first portion of the anchor. The at least one pivot axis is located beyond the outer periphery of the support structure when the first portion of the anchor extends through the transverse bore of the support structure.

According to another embodiment of the present invention, an orthopedic assembly is provided that includes a support structure and an anchor. The support structure is configured for securement to a femur, the support structure having an outer periphery and defining a transverse bore that extends through the support structure. The anchor is configured to extend through the transverse bore of the support structure, the anchor including a first portion having a first longitudinal axis and a second portion having a second longitudinal axis. The second portion of the anchor is moveably coupled to the first portion of the anchor to adjust an angle defined between the second longitudinal axis and the first longitudinal axis. The second portion of the anchor is located outside of the transverse bore of the support structure when the first portion of the anchor extends through the transverse bore of the support structure.

According to yet another embodiment of the present invention, a method is provided for stabilizing a fractured femur using an orthopedic assembly that includes a support structure having an outer periphery and an anchor having a first portion and a second portion moveably coupled to the first portion at a pivot location. The femur includes a shaft and a head that extends medially from the shaft. The method includes the steps of securing the support structure to the femur, inserting the anchor through the support structure, and moving the second portion of the anchor relative to the first portion of the anchor with the pivot location positioned beyond the outer periphery of the support structure.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 9 is an elevational view of another orthopedic assembly, including an intramedullary nail and another exemplary lag screw of the present invention, shown with the lag screw in a first angular orientation;

FIG. 10 is an elevational view of the orthopedic assembly of FIG. 9, shown with the lag screw in a second angular orientation;

FIG. 11 is a partial cross-sectional view of the orthopedic assembly of FIG. 9, shown with the lag screw in a straight orientation;

FIG. 12 is an elevational view of another orthopedic assembly, including an intramedullary nail and an exemplary blade assembly of the present invention, shown with the lag screw in a first angular orientation;

FIG. 13 is a cross-sectional view of the blade assembly of FIG. 12, taken along line 13-13 of FIG. 12;

FIG. 14 is a partial cross-sectional view of the blade assembly of FIG. 12, shown with the blade assembly in a straight orientation;

FIG. 15 is an elevational view of another exemplary blade assembly of the present invention;

FIG. 16 is a partial cross-sectional, top plan view of the blade assembly of FIG. 15, taken along line 16-16 of FIG. 15;

FIG. 17 is an elevational view of another exemplary blade assembly of the present invention;

FIG. 18 is a partial cross-sectional, top plan view of the blade assembly of FIG. 17, taken along line 18-18 of FIG. 17;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
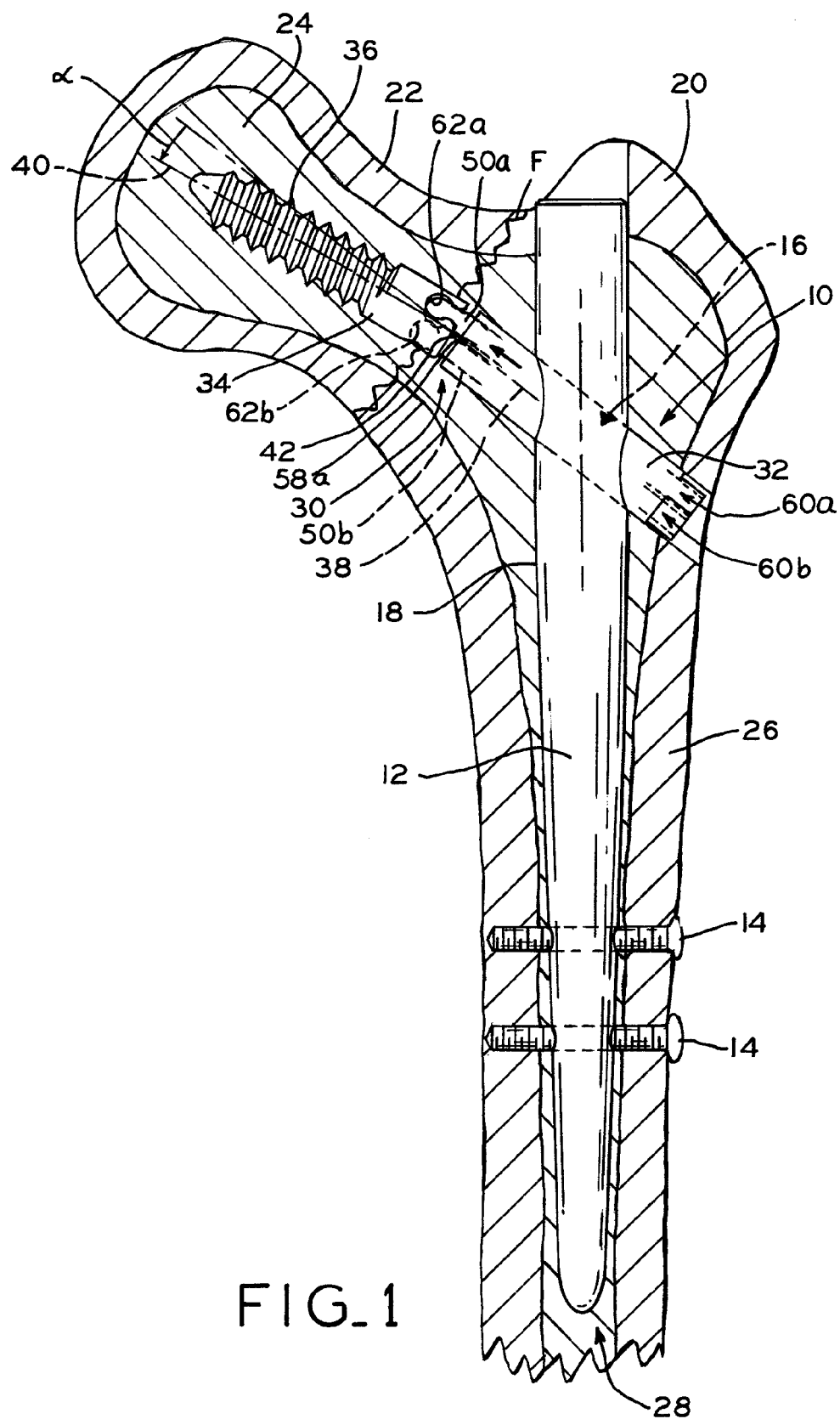
FIG. 1 is an elevational view of an orthopedic assembly, including an intramedullary nail and an exemplary lag screw of the present invention, shown with the lag screw implanted in a fractured femur in a first angular orientation.

Orthopedic assembly 10 may be used to align and stabilize fracture F of femur 20, as shown in FIG. 1. Exemplary orthopedic assemblies 10 of the present invention are particularly well-suited for treating fractures along the neck 22 of femur 20, in which head 24 of femur 20 is at least partially separated from shaft 26 of femur 20. As may be appreciated, the illustrated fracture F is merely representative, and other fracture patterns may be repaired using orthopedic assembly 10 of the present invention. Also, orthopedic assembly 10 may be utilized even in the absence of fracture F in femur 20, such as when femur 20 is weakened due to a congenital defect or disease, to support and stabilize femur 20.

In the illustrated embodiment of FIG. 1, orthopedic assembly 10 includes a support structure in the form of intramedullary nail 12 that is shown implanted into a prepared intramedullary canal 28 of femur 20 and secured in place with distal screws 14. It is also within the scope of the present invention that the support structure of orthopedic assembly 10 may include a bone plate (not shown) that is configured to be secured outside of femur 20, rather than inside intramedullary canal 28 of femur 20. Intramedullary nail 12 also includes transverse bore 16 and outer periphery 18, both of which are described further below.

Referring to FIGS. 1-8, orthopedic assembly 10 further includes an anchor in the form of lag screw 30. With lag screw 30 implanted into femur 20 along with intramedullary nail 12, lag screw 30 extends through transverse bore 16 of intramedullary nail 12. More particularly, and as shown in FIG. 1, lag screw 30 extends through transverse bore 16 of intramedullary nail 12 to extend through shaft 26 of femur 20, across fracture F in neck 22 of femur 20, and into head 24 of femur 20.

Lag screw 30 includes first portion 32 and second portion 34. As shown in FIG. 1, first portion 32 of lag screw 30 is positioned in shaft 26 of femur 20 and extends through transverse bore 16 of intramedullary nail 12. In this arrangement, the angular orientation of first portion 32 of lag screw 30 is fixed with respect to intramedullary nail 12. It is within the scope of the present invention that first portion 32 of lag screw 30 may be fixedly coupled to intramedullary nail 12, or that first portion 32 of lag screw 30 may be slidably coupled to intramedullary nail 12 to provide compression via axial translation of lag screw 30 through transverse bore 16 of intramedullary nail 12. Also, as shown in FIG. 1, second portion 34 of lag screw 30 extends from first portion 32 of lag screw 30 and through neck 22 and head 24 of femur 20. Second portion 34 of lag screw 30 includes external thread 36 to engage the bone of femur 20. With orthopedic assembly 10 implanted into femur 20, lag screw 30 and intramedullary nail 12 cooperate to anchor the fractured head 24 of femur 20 to shaft 26 of femur 20.

Figure 7:
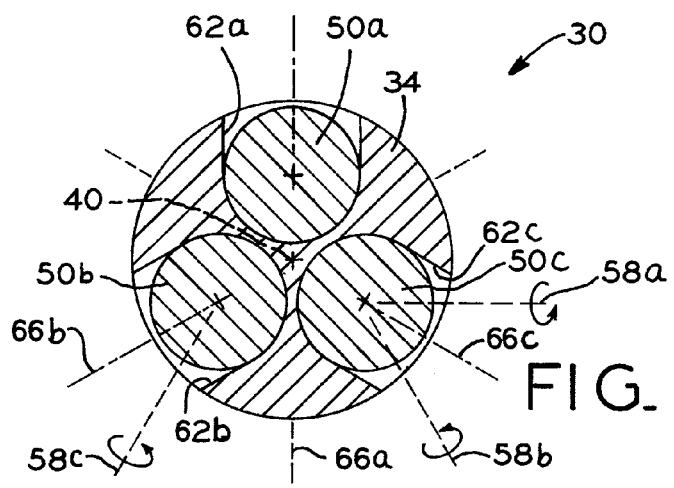
FIG. 7 is a cross-sectional view of the lag screw of FIG. 6, taken along line 7-7 of FIG. 6.

To adjust the angular orientation of lag screw 30 relative to intramedullary nail 12, second portion 34 of lag screw 30 is configured to move relative to first portion 32 of lag screw 30. First portion 32 of lag screw 30 remains in a fixed angular orientation with respect to intramedullary nail 12, extending through transverse bore 16 of intramedullary nail 12 along first longitudinal axis 38. Second portion 34 of lag screw 30 is configured to move relative to first portion 32 of lag screw 30 and intramedullary nail 12, such that second longitudinal axis 40 of second portion 34 is either aligned with or offset from first longitudinal axis 38 of first portion 32. To facilitate the following discussion, the point at which second longitudinal axis 40 of second portion 34 intersects first longitudinal axis 38 of first portion 32 is referred to herein as junction 42. According to an exemplary embodiment of the present invention, second portion 34 of lag screw 30 is configured to move relative to first portion 32 of lag screw 30 about at least one pivot axis. In the illustrated embodiment, second portion 34 of lag screw 30 is configured to move relative to first portion 32 of lag screw 30 about a plurality of pivot axes 58a, 58b, 58c, as shown in FIG. 7. Depending on the structure of lag screw 30, the pivot axis may or may not extend through junction 42.

Figure 3:
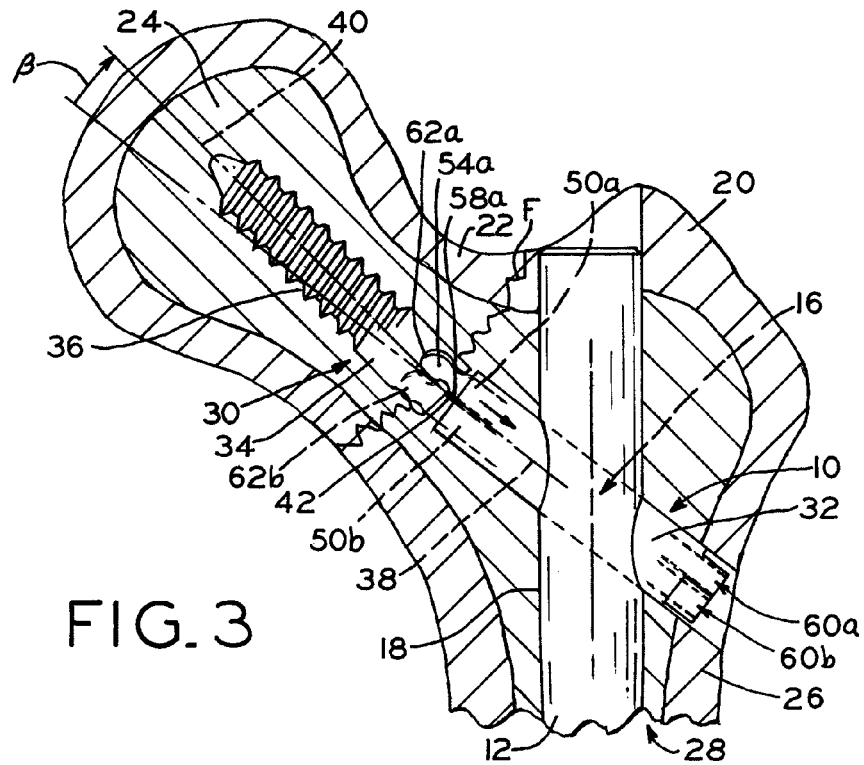
FIG. 3 is an elevational view of the orthopedic assembly of FIG. 1, shown with the lag screw implanted in the fractured femur in a second angular orientation.

In operation, the angular orientation of second portion 34 of lag screw 30 may be adjusted relative to first portion 32 of lag screw 30 to accommodate a patient's particular needs. For example, second portion 34 of lag screw 30 may be angled upward relative to first portion 32 of lag screw 30, as shown in FIG. 3, to resist downward anatomical forces on head 24 of femur 20, reducing the potential for head 24 to collapse relative to shaft 26 of femur 20.

According to an exemplary embodiment of the present invention, with first portion 32 lag screw 30 extending through transverse bore 16 of intramedullary nail 12, the pivot axis, such as pivot axis 58a of FIG. 1, is located beyond outer periphery 18 of intramedullary nail 12 and outside of transverse bore 16 of intramedullary nail 12.

Advantageously, locating the pivot axis beyond outer periphery 18 of intramedullary nail 12 allows for the use of standard attachment mechanisms between lag screw 30 and intramedullary nail 12 while still allowing at least a portion of lag screw 30 to move relative to intramedullary nail 12. In certain known devices in which the entire anchor is configured to move relative to a support structure, the support structure must be provided with a customized coupling or socket to accommodate the moveable anchor that extends therethrough.

Also advantageously, locating the pivot axis beyond outer periphery 18 of intramedullary nail 12 may reduce the area of femur 20 impacted by movement of lag screw 30. In certain known devices in which the entire anchor is configured to move relative to the support structure, the stationary bone that surrounds the movable anchor may be compromised. For example, bone that surrounds the drilled anchor hole, including bone of the lateral cortex located near the entry wound, may be compressed or removed to provide space for the movable anchor to move. As shown in FIG. 1, pivot axis 58*a* is located medially beyond outer periphery 18 of intramedullary nail 12. In this arrangement, the bone of femur 20 that surrounds intramedullary nail 12 and first portion 32 of lag screw 30, both of which retain a fixed angular orientation with respect to femur 20, is not substantially impacted by moving second portion 34 of lag screw 30. To further minimize the impact on the surrounding bone of femur 20, lag screw 30 may be provided in various lengths and configurations such that the pivot axis is substantially aligned with fracture F, as shown with respect to pivot axis 58*a* of FIG. 1. In this embodiment, moving second portion 34 of lag screw 30 relative to first portion 32 of lag screw 30 may allow for movement of femur 20 along fracture F without compromising the surrounding, stationary bone.

Figure 2:
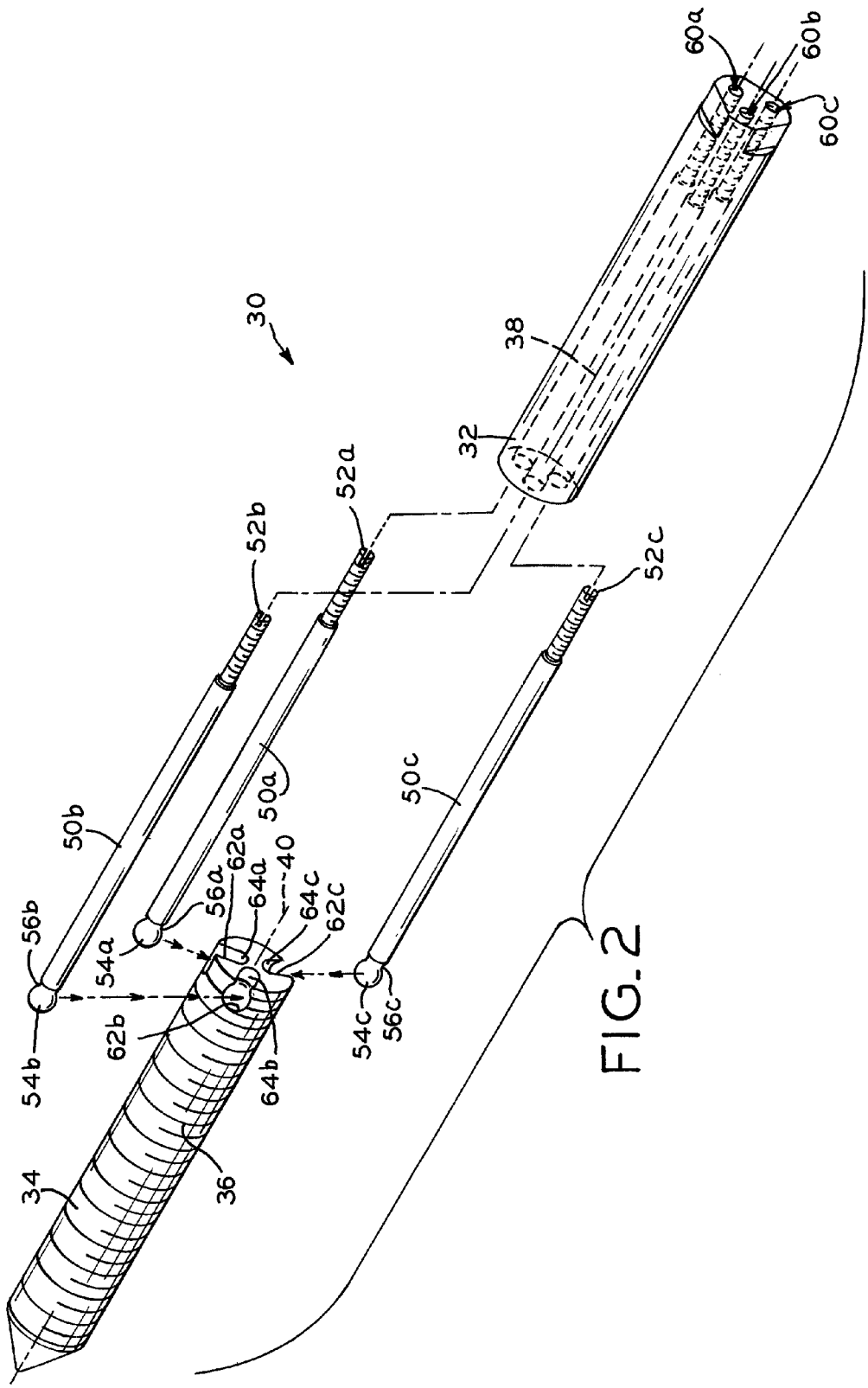
FIG. 2 is an exploded perspective view of the lag screw of FIG. 1.

Referring to FIGS. 1-8, second portion 34 of lag screw 30 is configured for angular movement relative to first portion 32 of lag screw 30 about a plurality of pivot axes 58*a*, 58*b*, 58*c*, to achieve movement in a plurality of planes 66*a*, 66*b*, 66*c*, respectively. In the illustrated embodiment, lag screw 30 includes a plurality of externally threaded adjustment rods 50*a*, 50*b*, 50*c*, each having engagement surface 52*a*, 52*b*, 52*c*, at one end and head 54*a*, 54*b*, 54*c*, and neck 56*a*, 56*b*, 56*c*, at the opposite end, as shown in FIG. 2. First portion 32 of lag screw 30 includes a plurality of internally threaded throughbores 60*a*, 60*b*, 60*c*, that are radially spaced an equal distance from first longitudinal axis 38. Second portion 34 of lag screw 30 includes a plurality of sockets 62*a*, 62*b*, 62*c*, that are radially spaced an equal distance from second longitudinal axis 40 to correspond with throughbores 60*a*, 60*b*, 60*c*, of first portion 32. Sockets 62*a*, 62*b*, 62*c*, of second portion 34 include tapered entrance walls 64*a*, 64*b*, 64*c*, as shown in FIG. 2. With threaded adjustment rods 50*a*, 50*b*, 50*c*, positioned within threaded throughbores 60*a*, 60*b*, 60*c*, of first portion 32, heads 54*a*, 54*b*, 54*c*, extend beyond first portion 32 and are received within sockets 62*a*, 62*b*, 62*c*, of second portion 34. Heads 54*a*, 54*b*, 54*c*, are configured to rotate within corresponding sockets 62*a*, 62*b*, 62*c*.

Rotating externally threaded adjustment rods 50*a*, 50*b*, 50*c*, in internally threaded throughbores 60*a*, 60*b*, 60*c*, causes adjustment rods 50*a*, 50*b*, 50*c*, to translate relative to first portion 32 of lag screw 30. For example, contacting engagement surface 52*a* with a screwdriver (not shown) and rotating adjustment rod 50*a* clockwise causes adjustment rod 50*a* to translate forward in throughbore 60*a* toward second portion 34 of lag screw 30, as shown in FIG. 1. Rotating adjustment rod 50*a* counter-clockwise causes adjustment rod 50*a* to translate backward in throughbore 60*a* away from second portion 34 of lag screw 30, as shown in FIG. 3.

Figure 6:
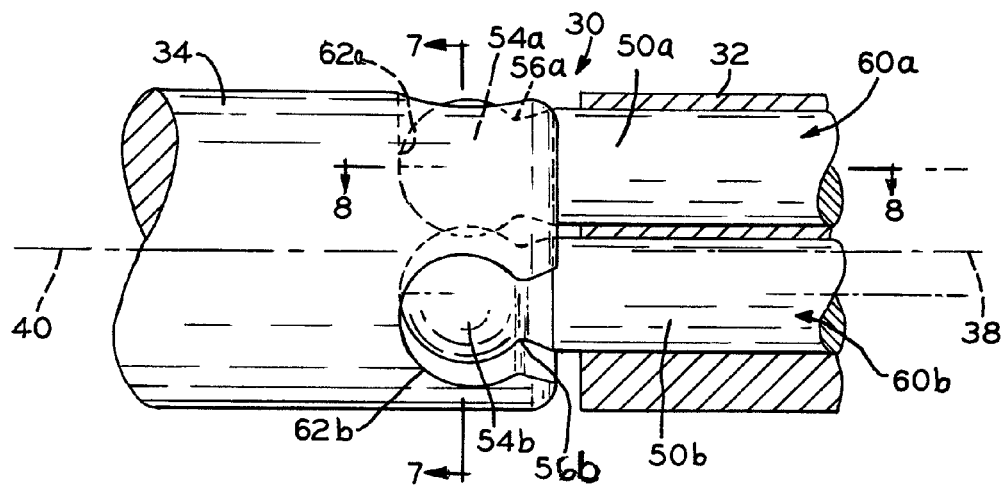
FIG. 6 is a partial cross-sectional view of the lag screw of FIG. 1, shown with the lag screw in a straight orientation.

In operation, second longitudinal axis 40 of second portion 34 may be aligned with first longitudinal axis 38 of first portion 32, or second longitudinal axis 40 of second portion 34 may be offset from first longitudinal axis 38 of first portion 32. With adjustment rods 50*a*, 50*b*, 50*c*, positioned in axial alignment, as shown in FIG. 6, lag screw 30 is oriented in a straight orientation such that first longitudinal axis 38 of first portion 32 is collinear with second longitudinal axis 40 of second portion 34. Moving all three adjustment rods 50*a*, 50*b*, 50*c*, forward in first portion 32 of lag screw 30, while maintaining adjustment rods 50*a*, 50*b*, 50*c* in axial alignment, will cause second portion 34 of lag screw 30 to move axially forward away from first portion 32 of lag screw 30. Similarly, moving all three adjustment rods 50*a*, 50*b*, 50*c*, backward into first portion 32 of lag screw 30, while maintaining adjustment rods 50*a*, 50*b*, 50*c* in axial alignment, will cause second portion 34 of lag screw 30 to move axially backward toward first portion 32 of lag screw 30.

On the other hand, with at least one adjustment rod 50*a*, 50*b*, 50*c*, positioned out of axial alignment with the others, second portion 34 of lag screw 30 may become angularly offset from first portion 32 of lag screw 30. Methods for adjusting the angular orientation of second portion 34 relative to first portion 32 of lag screw 30 are described below.

By translating adjustment rod 50*a*, second portion 34 may be oriented upward and downward relative to first portion 32 in plane 66*a* about pivot axis 58*a* (FIG. 7). As shown in FIG. 7, plane 66*a* extends through adjustment rod 50*a* and second longitudinal axis 40. With adjustment rod 50*a* translated axially forward of the other adjustment rods 50*b*, 50*c*, second portion 34 pivots downward about pivot axis 58*a* over heads 54*a*, 54*b*, 54*c*, to define angle alpha ($\alpha$) at junction 42 between second longitudinal axis 40 and first longitudinal axis 38, as shown in FIG. 1. With adjustment rod 50*a* translated backward of the other adjustment rods 50*b*, 50*c*, second portion 34 pivots upward about pivot axis 58*a* over heads 54*a*, 54*b*, 54*c*, to define angle beta ($\beta$) at junction 42 between second longitudinal axis 40 and first longitudinal axis 38, as shown in FIG. 3.

Figure 4:
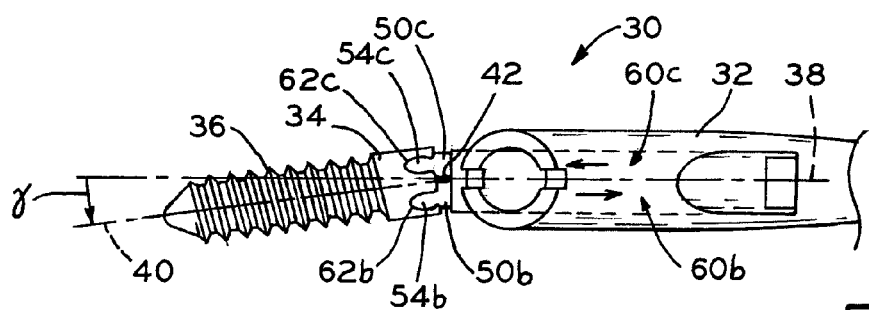
FIG. 4 is a top plan view of the lag screw of FIG. 1, shown with the lag screw in a third angular orientation.
Figure 5:
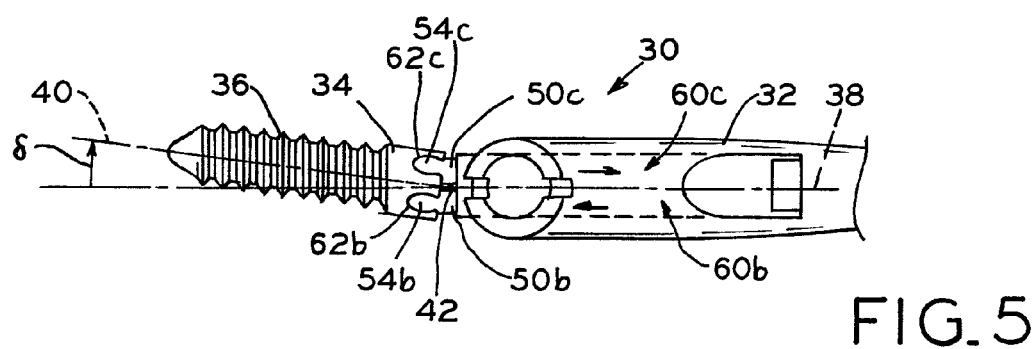
FIG. 5 is a top plan view of the lag screw of FIG. 1, shown with the lag screw in a fourth angular orientation.

By translating adjustment rod 50*b*, second portion 34 may be oriented side to side and upward and downward relative to first portion 32 in plane 66*b* about pivot axis 58*b* (FIG. 7). As shown in FIG. 7, plane 66*b* extends through adjustment rod 50*b* and second longitudinal axis 40. With adjustment rod 50*b* translated forward of the other adjustment rods 50*a*, 50*c*, second portion 34 pivots rightward and upward about pivot axis 58*b* over heads 54*a*, 54*b*, 54*c*, to define angle delta ($\delta$) at junction 42 between second longitudinal axis 40 and first longitudinal axis 38, as shown in FIG. 5. With adjustment rod 50*b* translated backward of the other adjustment rods 50*a*, 50*c*, second portion 34 pivots leftward and downward about pivot axis 58*b* over heads 54*a*, 54*b*, 54*c*, to define angle gamma ($\gamma$) at junction 42 between second longitudinal axis 40 and first longitudinal axis 38, as shown in FIG. 4.

By translating adjustment rod 50*c*, second portion 34 may be oriented side to side and upward and downward relative to first portion 32 in plane 66*c* about pivot axis 58*c* (FIG. 7). As shown in FIG. 7, plane 66*c* extends through adjustment rod 50*c* and second longitudinal axis 40. With adjustment rod 50*c* translated forward of the other adjustment rods 50*a*, 50*b*, second portion 34 pivots leftward and upward about pivot axis 58*c* over heads 54*a*, 54*b*, 54*c*, to define angle gamma ($\gamma$) at junction 42 between second longitudinal axis 40 and first longitudinal axis 38, as shown in FIG. 4. With adjustment rod 50*c* translated backward of the other adjustment rods 50*a*, 50*b*, second portion 34 pivots rightward and downward about pivot axis 58*c* over heads 54*a*, 54*b*, 54*c*, to define angle delta ($\delta$) at junction 42 between second longitudinal axis 40 and first longitudinal axis 38, as shown in FIG. 4.

Although second portion 34 of lag screw 30 is described above as being configured for axial movement and for pivotal movement in three planes 66*a*, 66*b*, 66*c*, relative to first portion 32 of lag screw 30, second portion 34 of lag screw 30 may also be oriented in other directions. For example, with adjustment rod 50*a* translated forward of adjustment rod 50*b* and adjustment rod 50*b* translated forward of adjustment rod 50*c*, second portion 34 pivots to an angular position between planes 66*a* and 66*c*.

Figure 8:
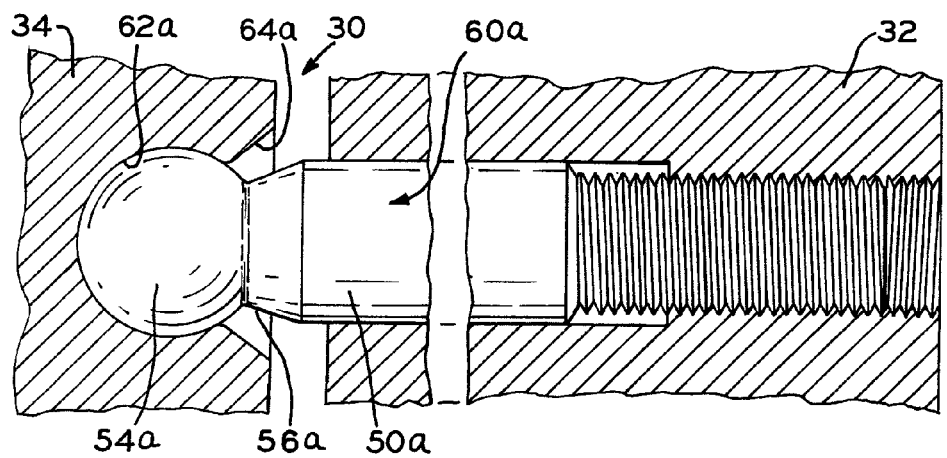
FIG. 8 is a partial cross-sectional view of the lag screw of FIG. 6.

As shown in FIG. 8, tapered entrance walls 64*a*, 64*b*, 64*c*, of sockets 62*a*, 62*b*, 62*c*, may cooperate with necks 56*a*, 56*b*, 56c, of adjustment rods 50a, 50b, 50c, to limit pivoting movement of adjustment rods 50a, 50b, 50c, in sockets 62a, 62b, 62c. As a result, the pivoting movement of second portion 34 relative to first portion 32 of lag screw 30 may be controlled.

Referring next to FIGS. 9-11, orthopedic assembly 100 includes an anchor in the form of lag screw 130 that is configured for angular adjustment within a plane. More particularly, second portion 134 of lag screw 130 is configured for angular adjustment relative to first portion 32 of lag screw 30 within a plane about pivot axis or pin 158. Lag screw 130 functions similarly to lag screw 30 of FIGS. 1-8, with like numerals indicating like elements. For example, first portion 132 of lag screw 130 may extend through transverse bore 16 of intramedullary nail 12, with second portion 134 of lag screw 130 extending from first portion 132 of lag screw 130 and into head 24 of femur 20 (FIG. 1).

In the illustrated embodiment, lag screw 130 includes an externally threaded adjustment rod 150. Adjustment rod 150 includes engagement surface 152 at one end and head 154 and neck 156 at the opposite end. First portion 132 of lag screw 130 includes an internally threaded throughbore 160 that is radially spaced from first longitudinal axis 138. Second portion 134 of lag screw 130 includes socket 162 that is radially spaced from second longitudinal axis 140 to correspond with throughbore 160. Socket 162 includes tapered entrance walls 164, as shown in FIG. 11. With threaded adjustment rod 150 positioned within threaded throughbore 160 of first portion 132, head 154 extends beyond first portion 132 and is received within socket 162 of second portion 134. Head 154 is configured to rotate within socket 162.

Rotating externally threaded adjustment rod 150 in internally threaded throughbore 160 causes adjustment rod 150 to translate relative to first portion 132 of lag screw 130. For example, contacting engagement surface 152 with a screwdriver (not shown) and rotating adjustment rod 150 clockwise causes adjustment rod 150 to translate forward in throughbore 160 toward second portion 134 of lag screw 130, as shown in FIG. 10. Rotating adjustment rod 150 counter-clockwise causes adjustment rod 150 to translate backward in throughbore 160 away from second portion 134 of lag screw 130, as shown in FIG. 9.

In operation, second longitudinal axis 140 of second portion 134 may be aligned with first longitudinal axis 138 of first portion 132, as shown in FIG. 11, or second longitudinal axis 140 of second portion 134 may be offset from first longitudinal axis 138 of first portion 132. In the illustrated embodiment of FIGS. 9-10, second portion 134 may be oriented upward and downward relative to first portion 132 by translating adjustment rod 150. With adjustment rod 150 translated forward relative to first portion 132, second portion 134 pivots upward about pivot pin 158 to define angle beta ($\beta$) at junction 142 between second longitudinal axis 140 and first longitudinal axis 138, as shown in FIG. 10. With adjustment rod 150 translated backward relative to first portion 132, second portion 134 pivots downward about pivot pin 158 to define angle alpha ($\alpha$) at junction 142 between second longitudinal axis 140 and first longitudinal axis 138, as shown in FIG. 9.

Referring next to FIGS. 12-14, orthopedic assembly 200 includes an anchor in the form of blade assembly 270 that is configured for angular adjustment within a plane. More particularly, second portion 234 of blade assembly 270 is configured for angular adjustment relative to first portion 232 of blade assembly 270 within a plane about pivot axis or pin 258. Blade assembly 270 functions similarly to lag screw 30 of FIGS. 1-8 and lag screw 130 of FIGS. 9-11, with like numerals indicating like elements. For example, first portion 232 of blade assembly 270 may extend through transverse bore 16 of intramedullary nail 12, with second portion 234 of blade assembly 270 extending from first portion 232 of blade assembly 270 and into head 24 of femur 20 (FIG. 1). However, unlike lag screw 30 of FIGS. 1-8 and lag screw 130 of FIGS. 9-11 which include external, helical threads 36, 136, respectively, blade assembly 270 includes axial projections 272 that extend from second portion 234 of blade assembly 270 to engage the bone of femur 20 (FIG. 1).

In the illustrated embodiment, blade assembly 270 includes an externally threaded adjustment rod 250. Adjustment rod 250 includes engagement surface 252 at one end and head 254 and neck 256 at the opposite end. First portion 232 of blade assembly 270 includes an internally threaded throughbore 260 that is radially spaced from first longitudinal axis 238. Second portion 234 of blade assembly 270 includes socket 262 that is radially spaced from second longitudinal axis 240 to correspond with throughbore 260. Socket 262 includes tapered entrance walls 264, as shown in FIG. 14. With threaded adjustment rod 250 positioned within threaded throughbore 260 of first portion 232, head 254 extends beyond first portion 232 and is received within socket 262 of second portion 234. Head 254 is configured to rotate within socket 262.

Rotating externally threaded adjustment rod 250 in internally threaded throughbore 260 causes adjustment rod 250 to translate relative to first portion 232 of blade assembly 270. For example, contacting engagement surface 252 with a screwdriver (not shown) and rotating adjustment rod 250 clockwise causes adjustment rod 250 to translate forward in throughbore 260 toward second portion 234 of blade assembly 270, as shown in FIG. 12. Rotating adjustment rod 250 counter-clockwise causes adjustment rod 250 to translate backward in throughbore 260 away from second portion 234 of blade assembly 270.

In operation, second longitudinal axis 240 of second portion 234 may be aligned with first longitudinal axis 238 of first portion 232, as shown in FIG. 14, or second longitudinal axis 240 of second portion 234 may be offset from first longitudinal axis 238 of first portion 232. With adjustment rod 250 translated forward relative to first portion 232, second portion 234 pivots upward about pivot pin 258 to define angle beta ($\beta$) at junction 242 between second longitudinal axis 240 and first longitudinal axis 238, as shown in FIG. 12. With adjustment rod 250 translated backward relative to first portion 232, second portion 234 pivots downward about pivot pin 258.

Referring next to FIGS. 15-16, orthopedic assembly 300 includes an anchor in the form of blade assembly 370 that is configured for angular adjustment within a plane. More particularly, second portion 334 of blade assembly 370 is configured for angular adjustment relative to first portion 332 of blade assembly 370 within a plane about pivot axis or pin 358. Blade assembly 370 functions similarly to lag screw 30 of FIGS. 1-8, lag screw 130 of FIGS. 9-11, and blade assembly 270 of FIGS. 12-14, with like numerals indicating like elements. For example, first portion 332 of blade assembly 370 may extend through transverse bore 16 of intramedullary nail 12 (FIG. 1), with second portion 334 of blade assembly 370 extending from first portion 332 of blade assembly 370 and into head 24 of femur 20 (FIG. 1).

In the illustrated embodiment, blade assembly 370 includes adjustment rod 350 having engagement surface 352 at one end and driving bevel gear 380 at the opposite end. First portion 332 of blade assembly 370 includes throughbore 360 that is shown extending along first longitudinal axis 338. Second portion 334 of blade assembly 370 includes engaging bevel gear 382 that extends about pivot pin 358. With adjustment rod 350 positioned within throughbore 360 of first portion 332, driving bevel gear 380 faces second portion 334 of blade assembly 370 and is oriented at a right angle relative to engaging bevel gear 382 to engage engaging bevel gear 382.

Rotating adjustment rod 350 in throughbore 360 causes driving bevel gear 380 to engage and rotate engaging bevel gear 382, as shown in FIG. 15. For example, contacting engagement surface 352 of adjustment rod 350 with a screwdriver (not shown) and rotating adjustment rod 350 clockwise causes both driving bevel gear 380 and engaging bevel gear 382 to rotate clockwise. Rotating adjustment rod 350 counter-clockwise causes both driving bevel gear 380 and engaging bevel gear 382 to rotate counter-clockwise.

In operation, second longitudinal axis 340 of second portion 334 may be aligned with first longitudinal axis 338 of first portion 332, as shown in FIG. 15, or second longitudinal axis 340 of second portion 334 may be offset from first longitudinal axis 338 of first portion 332. In the illustrated embodiment of FIG. 15, second portion 334 may be oriented upward and downward relative to first portion 332 by rotating adjustment rod 350. With adjustment rod 350 rotated clockwise, second portion 334 rotates clockwise and pivots upward about pivot pin 358 to define angle beta ($\beta$) at junction 342 between second longitudinal axis 340' and first longitudinal axis 338, as shown in FIG. 15. With adjustment rod 350 rotated counter-clockwise, second portion 334 rotates counter-clockwise and pivots downward about pivot pin 358 to define angle alpha ($\alpha$) at junction 342 between second longitudinal axis 340" and first longitudinal axis 338, as shown in FIG. 15.

Referring next to FIGS. 17-18, orthopedic assembly 400 includes an anchor in the form of blade assembly 470 that is configured for angular adjustment within a plane. More particularly, second portion 434 of blade assembly 470 is configured for angular adjustment relative to first portion 432 of blade assembly 470 within a plane about pivot axis or pin 458. Blade assembly 470 functions similarly to lag screw 30 of FIGS. 1-8, lag screw 130 of FIGS. 9-11, blade assembly 270 of FIGS. 12-14, and blade assembly 370 of FIGS. 15-16, with like numerals indicating like elements. For example, first portion 432 of blade assembly 470 may extend through transverse bore 16 of intramedullary nail 12 (FIG. 1), with second portion 434 of blade assembly 470 extending from first portion 432 of blade assembly 470 and into head 24 of femur 20 (FIG. 1).

In the illustrated embodiment, blade assembly 470 includes adjustment rod 450 having an engagement surface (not shown) at one end. At the end opposite the engagement surface, adjustment rod 450 includes annular channel 489 and a screw or worm 484. First portion 432 of blade assembly 470 includes throughbore 460 that is shown radially spaced from first longitudinal axis 438. Second portion 434 of blade assembly 470 is coupled to a wheel or worm gear 486 that extends about pivot pin 458. With adjustment rod 450 positioned within throughbore 460 of first portion 432, worm 484 faces second portion 434 of blade assembly 470 and is oriented to engage worm gear 486.

Rotating adjustment rod 450 in throughbore 460 causes worm 484 to engage and rotate worm gear 486, as shown in FIG. 17. For example, contacting the engagement surface (not shown) of adjustment rod 450 with a screwdriver (not shown) and rotating adjustment rod 450 clockwise may cause worm gear 486 to rotate clockwise. Rotating adjustment rod 450 counter-clockwise may cause worm gear 486 to rotate counter-clockwise. As shown in FIG. 17, annular flange 488 of first portion 432 protrudes into annular channel 489 of adjustment rod 450, allowing adjustment rod 450 to rotate in throughbore 460 while preventing adjustment rod 450 from retracting into throughbore 460.

In operation, second longitudinal axis 440 of second portion 434 may be aligned with first longitudinal axis 438 of first portion 432, as shown in FIG. 17, or second longitudinal axis 440 of second portion 434 may be offset from first longitudinal axis 438 of first portion 432. In the illustrated embodiment of FIG. 17, second portion 434 may be oriented upward and downward relative to first portion 432 by rotating adjustment rod 450. With adjustment rod 450 rotated clockwise, second portion 434 may rotate clockwise and pivot upward about pivot pin 458 to define angle beta ($\beta$) at junction 442 between second longitudinal axis 440' and first longitudinal axis 438, as shown in FIG. 17. With adjustment rod 450 rotated counter-clockwise, second portion 434 may rotate counter-clockwise and pivot downward about pivot pin 458 to define angle alpha ($\alpha$) at junction 442 between second longitudinal axis 440" and first longitudinal axis 438, as shown in FIG. 17.

Referring next to FIGS. 19-22, orthopedic assembly 500 includes an anchor in the form of blade assembly 570 that is configured for angular adjustment within a plane. More particularly, second portion 534 of blade assembly 570 is configured for angular adjustment relative to first portion 532 of blade assembly 570 within a plane about pivot axis or pin 558. Blade assembly 570 functions similarly to lag screw 30 of FIGS. 1-8, lag screw 130 of FIGS. 9-11, blade assembly 270 of FIGS. 12-14, blade assembly 370 of FIGS. 15-16, and blade assembly 470 of FIGS. 17-18, with like numerals indicating like elements. For example, first portion 532 of blade assembly 570 may extend through transverse bore 16 of intramedullary nail 12, with second portion 534 of blade assembly 570 extending from first portion 532 of blade assembly 570, wrapping around intramedullary nail 12, and extending into head 24 of femur 20 (FIG. 1).

In the illustrated embodiment, second portion 534 of blade assembly 570 includes a plurality of axially extending fingers 574. Fingers 574 of second portion 534 are coupled together via pivot pin 558 that extends through first portion 532 of blade assembly 570 in a direction perpendicular to first longitudinal axis 538 to pivotally couple fingers 574 of second portion 534 to first portion 532. Blade assembly 570 also includes adjustment rod 550 having engagement surface 552 at one end and screw or worm 584 and head 589 at the opposite end. First portion 532 of blade assembly 570 includes throughbore 560. Second portion 534 of blade assembly 570 is coupled to a wheel or worm gear 586 that extends about pivot pin 558. With adjustment rod 550 positioned within throughbore 560 of first portion 532, worm 584 is oriented to engage worm gear 586 of second portion 534.

Figure 21:
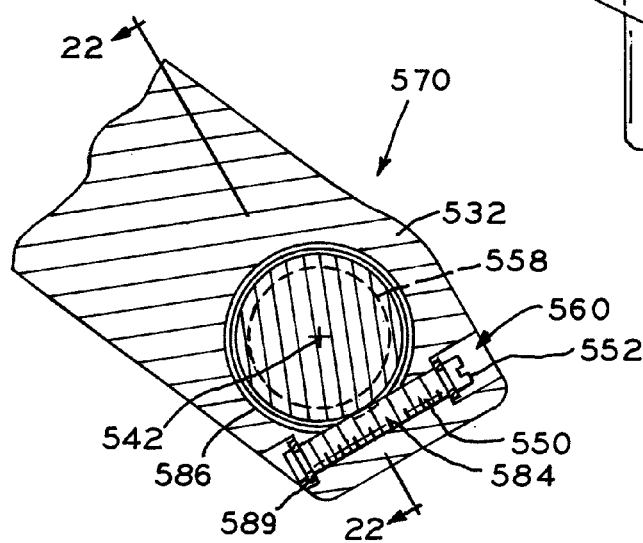
FIG. 21 is a cross-sectional view of the blade assembly of FIG. 19, taken along line 21-21 of FIG. 19.
Figure 22:
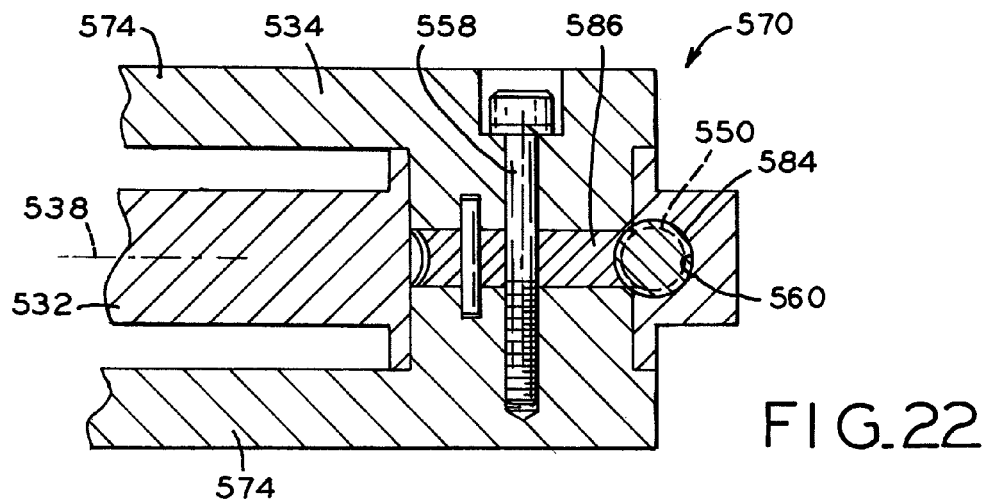
FIG. 22 is a cross-sectional view of the blade assembly of FIG. 21, taken along line 22-22 of FIG. 21.

Rotating adjustment rod 550 in throughbore 560 causes worm 584 to engage and rotate worm gear 586, as shown in FIG. 21. For example, contacting engagement surface 552 of adjustment rod 550 with a screwdriver (not shown) and rotating adjustment rod 550 clockwise may cause worm gear 586 to rotate clockwise. Rotating adjustment rod 550 counter-clockwise may cause worm gear 586 to rotate counter-clockwise. As shown in FIG. 21, head 589 of adjustment rod 550 prevents adjustment rod 550 from retracting into throughbore 560 of first portion 532 during this rotation step, because head 589 is larger in diameter than throughbore 560.

Figure 19:
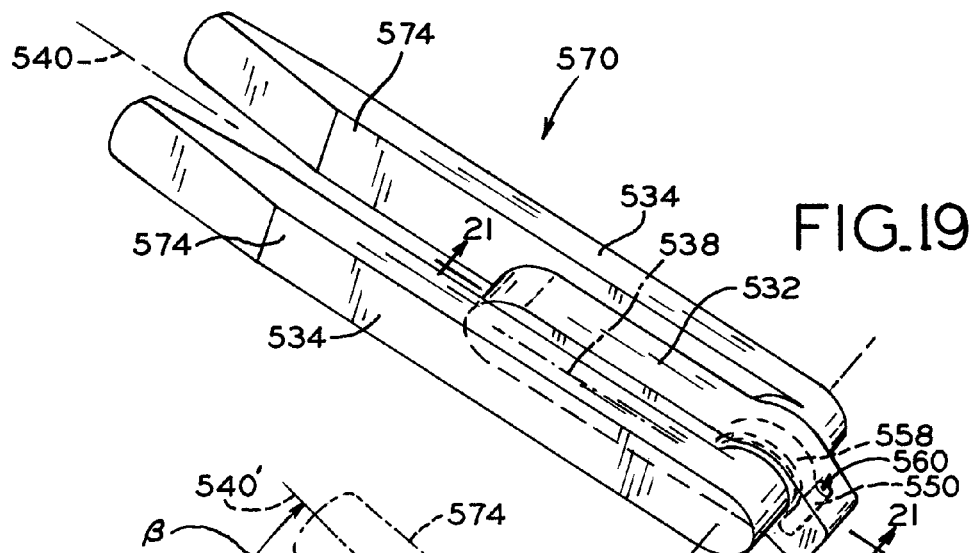
FIG. 19 is a perspective view of another exemplary blade assembly of the present invention, shown with the blade assembly in a straight orientation.
Figure 20:
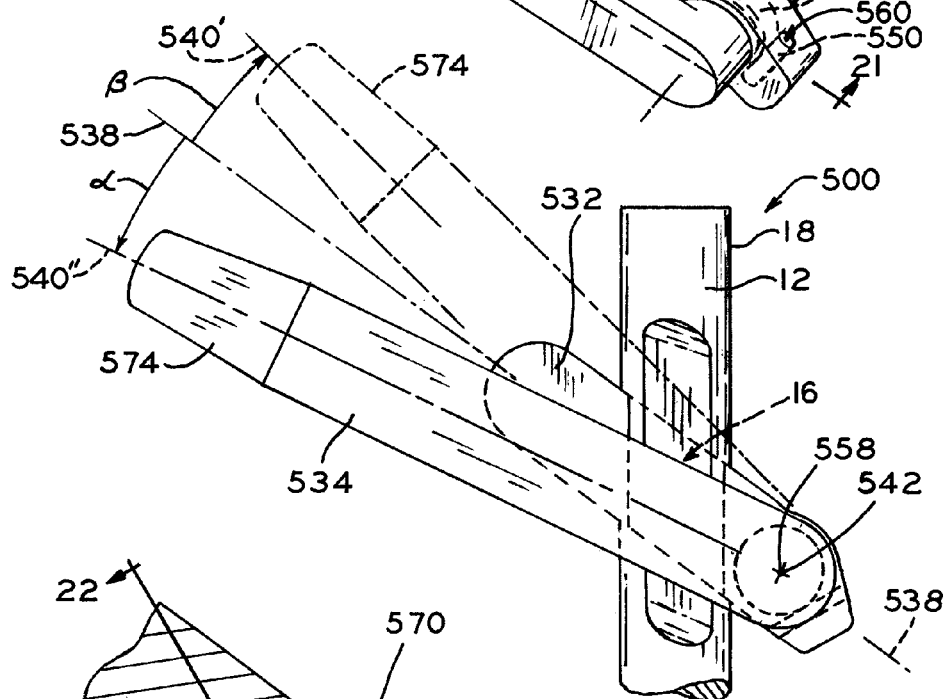
FIG. 20 is an elevational view of the blade assembly of FIG. 19 coupled to an intramedullary nail, shown with the blade assembly in a first angular orientation in solid lines and a second angular orientation in phantom.

In operation, second longitudinal axis 540 of second portion 534 may be aligned with first longitudinal axis 538 of first portion 532, as shown in FIG. 19. Alternatively, second longitudinal axis 540 of second portion 534 may be offset from first longitudinal axis 538 of first portion 532. In the illustrated embodiment of FIGS. 20-21, second portion 534 may be oriented upward and downward relative to first portion 532 by rotating adjustment rod 550. With adjustment rod 550 rotated clockwise, second portion 534 may rotate clockwise and pivot upward about pivot pin 558 to define angle beta (β) at junction 542 between second longitudinal axis 540' and first longitudinal axis 538, as shown in phantom in FIG. 20. With adjustment rod 550 rotated counter-clockwise, second portion 534 may rotate counter-clockwise and pivot downward about pivot pin 558 to define angle alpha (α) at junction 542 between second longitudinal axis 540" and first longitudinal axis 538, as shown in solid lines in FIG. 20.

Figure 23:
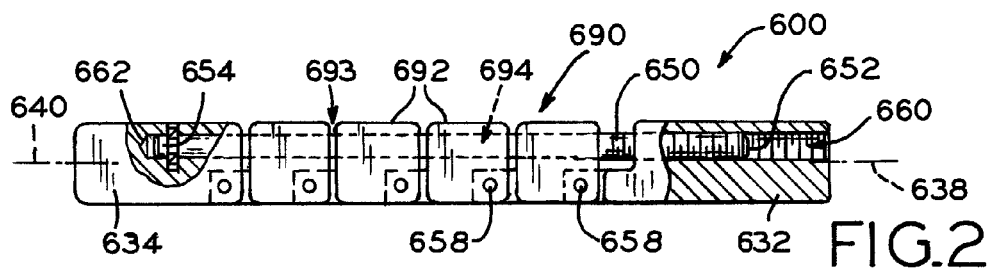
FIG. 23 is an elevational view of a flexible shaft of the present invention, shown with the flexible shaft in a straight orientation.
Figure 24:
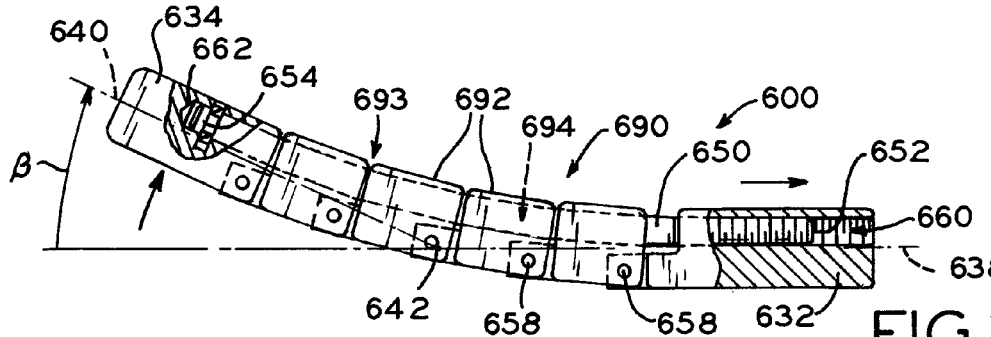
FIG. 24 is an elevational view of the flexible shaft of FIG. 23, shown with the flexible shaft in a first angular orientation.
Figure 25:
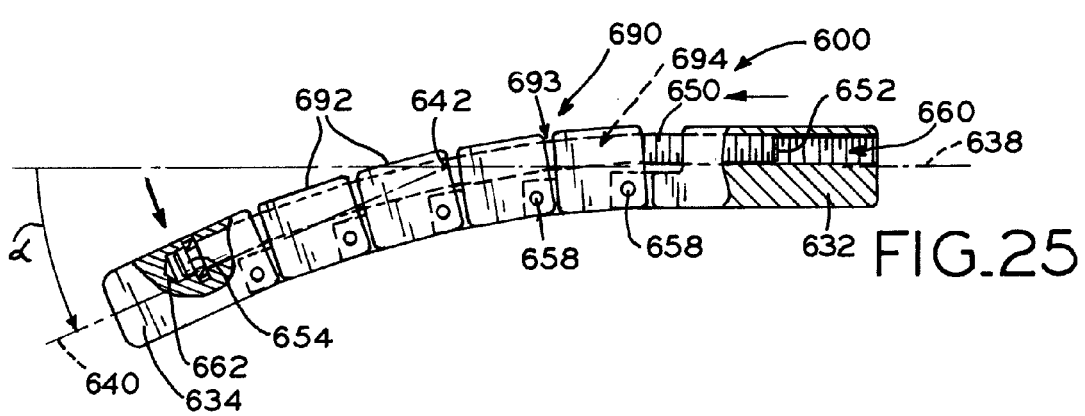
FIG. 25 is an elevational view of the flexible shaft of FIG. 23, shown with the flexible shaft in a second angular orientation.

Referring next to FIGS. 23-25, orthopedic assembly 600 includes an anchor in the form of flexible shaft 690 that is configured for angular adjustment within a plane. More particularly, second portion 634 of flexible shaft 690 is configured for angular adjustment relative to first portion 632 of flexible shaft 690 within a plane about a plurality of pivot axes or pins 658. Flexible shaft 690 functions similarly to lag screw 30 of FIGS. 1-8, lag screw 130 of FIGS. 9-11, blade assembly 270 of FIGS. 12-14, blade assembly 370 of FIGS. 15-16, blade assembly 470 of FIGS. 17-18, and blade assembly 570 of FIGS. 19-22, with like numerals indicating like elements. For example, first portion 632 of flexible shaft 690 may extend through transverse bore 16 of intramedullary nail 12 (FIG. 1), with second portion 634 of flexible shaft 690 extending from first portion 632 of flexible shaft 690 and into head 24 of femur 20 (FIG. 1).

In the illustrated embodiment, flexible shaft 690 includes a flexible, externally threaded adjustment rod 650 having engagement surface 652 at one end and head 654 at the opposite end. First portion 632 of flexible shaft 690 includes an internally threaded throughbore 660 that is radially spaced from first longitudinal axis 638. Second portion 634 of flexible shaft 690 includes socket 662 that is radially spaced from second longitudinal axis 640 to correspond with throughbore 660. With flexible adjustment rod 650 positioned within threaded throughbore 660 of first portion 632, head 654 extends beyond first portion 632 and is received within socket 662 of second portion 634. Head 654 is configured to rotate within socket 662.

As shown in FIGS. 23-25, flexible shaft 690 further includes a plurality of discrete shaft segments 692 located between first portion 632 and second portion 634. Although flexible shaft 690 is illustrated as having four shaft segments 692, flexible shaft 690 may be provided with any number of shaft segments 692. Each shaft segment 692 includes throughbore 694. As shown in FIG. 23, threaded throughbore 660 of first portion 632, throughbores 694 of each shaft segment 692, and socket 662 of second portion 634 are axially aligned such that flexible adjustment rod 650 extends through flexible shaft 690 to link first portion 632, shaft segments 692, and second portion 634 of flexible shaft 690. Adjacent components of flexible shaft 690 are separated by voids 693. Also, adjacent components of flexible shaft 690 are coupled together via pivot pins 658, each pivot pin 658 extending in a direction substantially perpendicular to first longitudinal axis 638 of first portion 632.

Rotating the flexible, externally threaded adjustment rod 650 in internally threaded throughbore 660 causes adjustment rod 650 to translate relative to first portion 632 of flexible shaft 690. For example, contacting engagement surface 652 with a screwdriver (not shown) and rotating adjustment rod 650 clockwise causes adjustment rod 650 to translate forward in throughbore 660 toward second portion 634 of flexible shaft 690, as shown in FIG. 25. Rotating adjustment rod 650 counter-clockwise causes adjustment rod 650 to translate backward in throughbore 660 away from second portion 634 of flexible shaft 690, as shown in FIG. 24. Head 654 prevents adjustment rod 650 from retracting out of socket 662 of second portion 634 during this translation step.

In operation, second longitudinal axis 640 of second portion 634 may be aligned with first longitudinal axis 638 of first portion 632, as shown in FIG. 23. For example, with flexible adjustment rod 650 positioned in a straight orientation, first longitudinal axis 638 of first portion 632 may be collinear with second longitudinal axis 640 of second portion 634.

Alternatively, second longitudinal axis 640 of second portion 634 may be offset from first longitudinal axis 638 of first portion 632, as shown in FIGS. 24-25. For example, second portion 634 may be oriented upward and downward relative to first portion 632. With adjustment rod 650 translated forward in throughbore 660 relative to first portion 632, head 654 of adjustment rod 650 forces second portion 634 away from first portion 632. As a result, second portion 634 and shaft segments 692 pivot downward about pivot pins 658 to define angle alpha (α) at junction 642 between second longitudinal axis 640 and first longitudinal axis 638, as shown in FIG. 25. With adjustment rod 650 translated backward in throughbore 660 relative to first portion 632, head 654 of adjustment rod 650 pulls second portion 634 toward first portion 632. As a result, second portion 634 and shaft segments 692 pivot upward about pivot pins 658 to define angle beta (β) at junction 642 between second longitudinal axis 640 and first longitudinal axis 638, as shown in FIG. 24. Although the embodiment depicted in FIGS. 23-25 includes one flexible adjustment rod 650, flexible shaft 690 may be provided with a plurality of flexible adjustment rods 650 to accommodate angular motion in various dimensions.

Flexible shaft 690, including second portion 634 of flexible shaft 690, may include external threads or other suitable protrusions (not shown) to engage the bone of femur 20 (FIG. 1). For example, a threaded tip (not shown) may be coupled to second portion 634 of flexible shaft 690 to engage the bone of femur 20 (FIG. 1). Alternatively, flexible shaft 690 may be cannulated and configured to receive a suitable device for engaging the bone of femur 20 (FIG. 1).

Flexible shaft 690 may be of the type disclosed in U.S. patent application Ser. No. 11/244,640, filed Oct. 6, 2005, entitled "FLEXIBLE SHAFT," the disclosure of which is expressly incorporated by reference herein.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopedic assembly comprising:
   a support structure, configured for securement to a bone, having an outer periphery and defining a transverse bore that extends therethrough; and
   an anchor longitudinally extending from a first portion comprising a first longitudinal axis to a second portion comprising a second longitudinal axis and having an intermediate portion therebetween, the first portion configured to extend through the transverse bore in a fixed angular orientation relative to the support structure and including a first terminal end, the second portion including a second terminal end opposite the first terminal end, and the intermediate portion including a pivot location provided by an adjustment mechanism,
   the adjustment mechanism, at the pivot location, movably coupling the second portion of the anchor relative to the first portion of the anchor allowing the second terminal end to move about at least one pivot axis relative to the first portion of the anchor, the at least one pivot axis being located beyond the outer periphery of the support structure when the first portion of the anchor extends through the transverse bore of the support structures;

wherein the pivot location is configured to allow the second longitudinal axis to be collinear with the first longitudinal axis in a straight anchor configuration and to be non-collinear with the first longitudinal axis in an angled anchor configuration.

2. The orthopedic assembly of claim 1, wherein the second portion of the anchor is coupled, at the pivot location, to the first portion of the anchor for movement in at least one plane.

3. The orthopedic assembly of claim 1, wherein the at least one pivot axis is located medially beyond the outer periphery of the support structure when the support structure is secured to the bone.

4. The orthopedic assembly of claim 1, wherein the adjustment mechanism of the anchor includes at least one adjustment rod configured to translate through the first portion of the anchor to move the second portion of the anchor.

5. The orthopedic assembly of claim 1, wherein the adjustment mechanism of the anchor includes at least one rotatable adjustment rod configured to engage a gear to move the second portion of the anchor.

6. The orthopedic assembly of claim 1, wherein the support structure includes an intramedullary nail disposed entirely within an outer periphery of the bone.

7. The orthopedic assembly of claim 1, wherein the anchor consists of one of a lag screw and a blade.

8. The orthopedic assembly of claim 1, wherein the second portion of the anchor is threaded, the threaded second portion of the anchor being movably coupled to the first portion of the anchor at the pivot location.

9. The orthopedic assembly of claim 1, wherein the at least one pivot axis is located at a junction included in the intermediate portion of the anchor, between the first and second portions of the anchor.

10. An orthopedic assembly comprising:
a support structure, configured for securement to a bone, having an outer periphery and defining a transverse bore that extends therethrough; and
an anchor, configured to extend through the transverse bore of the support structure, having a straight configuration and an angled configuration, the anchor comprising:
a first portion defining a first longitudinal axis, wherein the first portion of the anchor extends through the transverse bore of the support structure in a fixed angular orientation to define a fixed angle between the first longitudinal axis and the support structure,
a second portion defining a second longitudinal axis, and
an intermediate portion between the first and second portions and including a pivot location, the pivot location configured to allow the second longitudinal axis to be collinear with the first longitudinal axis in the straight configuration and to allow the second portion of the anchor to move relative to the first portion of the anchor to angle the second longitudinal axis relative to the first longitudinal axis in the angled configuration, the second portion of the anchor being located outside of the transverse bore of the support structure when the first portion of the anchor extends through the transverse bore of the support structure.

11. The orthopedic assembly of claim 10, wherein the second portion of the anchor is located beyond the outer periphery of the support structure when the first portion of the anchor extends through the transverse bore of the support structure.

12. The orthopedic assembly of claim 10, wherein the first portion of the anchor projects outwardly from the transverse bore of the support structure to a terminal end located beyond the outer periphery of the support structure, the second portion of the anchor being moveably coupled, at the pivot location, to the terminal end of the first portion of the anchor.

13. The orthopedic assembly of claim 10, wherein the second portion of the anchor is configured to pivot about at least one pivot axis relative to the first portion of the anchor, the at least one pivot axis being radially offset from the first longitudinal axis.

14. The orthopedic assembly of claim 10, wherein the second portion of the anchor is configured to pivot about at least one pivot axis relative to the first portion of the anchor, the at least one pivot axis extending substantially perpendicular to the first longitudinal axis.

15. The orthopedic assembly of claim 10, wherein an outer surface of the second portion of the anchor is encircled by bone to engage bone in both the straight configuration and the angled configuration.

16. The orthopedic assembly of claim 10, wherein a first end of the first portion of the anchor is moveably coupled to a second end of the second portion of the anchor at the pivot location.

17. A method of stabilizing a fractured bone, including a shaft and a head that extends medially from the shaft, using an orthopedic assembly, the method comprising the steps of:
securing a support structure to the shaft of the bone;
inserting a first portion of an anchor through a transverse bore of the support structure;
implanting a second portion of the anchor into the head of the bone; and
moving the head of the bone relative to the shaft of the bone by moving the second portion of the anchor relative to the first portion of the anchor using a pivot location positioned beyond the outer periphery of the support structure and between the first and second portions of the anchor.

18. The method of claim 17, wherein the inserting step comprises providing the anchor with the first and second portions aligned in a straight configuration.

19. The method of claim 17, wherein the inserting step consists of inserting the anchor with the pivot location positioned one of medially of the support structure and laterally of the support structure.

20. The method of claim 17, wherein the inserting step comprises substantially aligning the pivot location with a fracture line of the bone.

21. The method of claim 17, wherein the securing step consists of securing the support structure entirely within the shaft of the bone.

22. An orthopedic assembly for stabilizing a fractured bone, including a shaft and a head, the orthopedic assembly comprising:
a support structure, configured for securement to the shaft of the bone, having an outer periphery; and
an anchor comprising a first portion defining a first longitudinal axis, a second portion defining a second longitudinal axis, and an intermediate portion between the first and second portions, the intermediate portion including a pivot location positionable beyond the outer periphery of the support structure and spaced from both a first terminal end of the first portion and a second terminal end of the second portion, the pivot location configured to allow the second longitudinal axis to be collinear with the first longitudinal axis in a straight configuration and to allow the second portion to move relative to the first portion to angle the second longitudinal axis relative to the first longitudinal axis in an angled configuration, the first portion of the anchor couplable to the support structure and the second portion of the anchor couplable to the head of the bone such that, when the support structure and the anchor are implanted within the fractured bone, the head of the bone can be moved relative to the shaft of the bone about the pivot location included in the intermediate portion of the anchor.

23. The orthopedic assembly of claim 22, wherein the support structure consists of at least one of an intramedullary nail and a bone plate.

24. The orthopedic assembly of claim 22, wherein the anchor consists of one of a lag screw and a blade.

* * * * *

UNITED STATES PATENT AND TRADEMARK OFFICE
CERTIFICATE OF CORRECTION

PATENT NO. : 8,926,611 B2  
APPLICATION NO. : 12/558984  
DATED : January 6, 2015  
INVENTOR(S) : Keller et al.

Page 1 of 1

It is certified that error appears in the above-identified patent and that said Letters Patent is hereby corrected as shown below:

In the Claims

In column 13, line 5, in Claim 1, delete "structures" and insert --structure--, therefor Signed and Sealed this
Twenty-eighth Day of April, 2015

Michelle K. Lee
*Director of the United States Patent and Trademark Office*